United States Patent
Deutz et al.

(10) Patent No.: US 10,175,245 B2
(45) Date of Patent: Jan. 8, 2019

(54) METHODS FOR MEASURING FAT DIGESTIBILITY AND USES THEREOF

(71) Applicants: Nicolaas E. Deutz, College Station, TX (US); Marielle P. Engelen, College Station, TX (US); Guinur Com, Little Rock, AR (US); John J. Thaden, College Station, TX (US)

(72) Inventors: Nicolaas E. Deutz, College Station, TX (US); Marielle P. Engelen, College Station, TX (US); Guinur Com, Little Rock, AR (US); John J. Thaden, College Station, TX (US)

( * ) Notice: Subject to any disclaimer, the term of this patent is extended or adjusted under 35 U.S.C. 154(b) by 231 days.

(21) Appl. No.: 14/543,026

(22) Filed: Nov. 17, 2014

(65) Prior Publication Data

US 2015/0072366 A1  Mar. 12, 2015

Related U.S. Application Data

(63) Continuation of application No. 14/031,921, filed on Sep. 19, 2013, now Pat. No. 8,906,640.

(60) Provisional application No. 61/703,582, filed on Sep. 20, 2012.

(51) Int. Cl.
*G01N 33/58* (2006.01)
*G01N 33/92* (2006.01)
*G01N 33/50* (2006.01)
*C12Q 1/37* (2006.01)
*C12Q 1/61* (2006.01)
*C12Q 1/44* (2006.01)

(52) U.S. Cl.
CPC ............. *G01N 33/58* (2013.01); *C12Q 1/37* (2013.01); *C12Q 1/44* (2013.01); *C12Q 1/61* (2013.01); *G01N 33/5091* (2013.01); *G01N 33/92* (2013.01); *G01N 2458/15* (2013.01); *G01N 2800/04* (2013.01)

(58) Field of Classification Search
None
See application file for complete search history.

(56) References Cited

U.S. PATENT DOCUMENTS 4,444,879 A * 4/1984 Foster .................. G01N 33/545
422/400

FOREIGN PATENT DOCUMENTS

CA          1078865 A   *  6/1980  ............ C07D 309/12

OTHER PUBLICATIONS

Murphy et al. Metabolic handling of 13C labelled tripalmitin in healthy controls and patients with cystic fibrosis. 1998 Arch. Dis. Child. 79: 44-47.*
Bougnères et al. Stable isotope dilution method for measurement of palmitate content and labeled palmitate tracer enrichment in microliter plasma samples. 1982 J. Lipid Res. 23: 502-507.*
Binnert et al. Use of gas chromatography/isotope ratio-mass spectrometry to study triglyceride metabolism in humans. 1995 Lipids 30: 869-873.*

* cited by examiner

*Primary Examiner* — Michael G. Hartley
*Assistant Examiner* — Jennifer Lamberski
(74) *Attorney, Agent, or Firm* — Benjamin Aaron Adler

(57) ABSTRACT

The present invention provides methods for continuous measurement of triglyceride digestibility during a meal. A stable isotope labeled triglyceride and a free fatty acid tracer are added to the meal. The ratio between a ratio of isotope labeled fatty acid produced after digestion to free fatty acid tracer represents the percentage of digestion of triglycerides by lipase from the pancreas.

9 Claims, 7 Drawing Sheets

METHODS FOR MEASURING FAT DIGESTIBILITY AND USES THEREOF

CROSS-REFERENCE TO RELATED APPLICATION

This application is a divisional under 35 U.S.C. § 120 of pending non-provisional U.S. Ser. No. 14/031,921, filed Sep. 19, 2013, which claims benefit of priority under 35 U.S.C. § 119(e) of provisional application U.S. Ser. No. 61/703,582, filed Sep. 20, 2012, the entirety of which is hereby incorporated by reference.

BACKGROUND OF THE INVENTION

Field of the Invention

The present invention is in the field of nutrition. More specifically, the present invention is directed to methods of measuring protein and/or fat digestibility and uses thereof.

Description of the Related Art

Malabsorption of nutrients due to exocrine pancreatic insufficiency is a main factor contributing to weight loss or poor weight gain in patients with cystic fibrosis (CF) leading to deficiencies of essential nutrients. Although it is well established that fat digestibility is impaired in cystic fibrosis, the prior art methods to measure protein digestibility are limited and often not accurate. As impaired protein digestibility leads to an impaired anabolic response to a meal as well as to high loads of undigested proteins in the colon, which induce diarrhea and the production of harmful toxins by gut bacteria, accurate quantification of protein digestibility is of high clinical importance in cystic fibrosis.

Many decades ago, a diminished retention of dietary proteins in cystic fibrosis was demonstrated with nitrogen balance tests and stool analyses, methods with limited accuracy that are too laborious and time consuming for routine diagnostic use. In 1952, a simpler and accurate method was developed using oral ingestion of $^{131}$I-labeled protein. $^{13}$C intrinsically labeled milk or egg proteins has been used to assess protein digestibility by measuring the enrichment kinetics of labeled $CO_2$ in the breath in response to meal intake. A limitation of this method is the difficulty to obtain large amounts of proteins with sufficiently high amino acid enrichment levels and with adequate labeling patterns, making production of these labeled proteins cumbersome and expensive. Furthermore, the accuracy of using $^{13}$C-intrinsically labeled milk or egg protein, or even uniformly $^{13}$C-labeled algal protein and measuring $^{13}CO_2$ production might be limited in cystic fibrosis as these patients are characterized by chronic and acute episodes of lung inflammation which contribute to $CO_2$ production in the breath and changes in the $CO_2$ pool size.

Reduced digestion capacity of nutrients due to exocrine pancreatic insufficiency (EPI) is an important disease-related factor contributing to weight loss. Severe exocrine pancreatic insufficiency impairs the digestion of fat, carbohydrate and protein leading to nutrient deficiencies. Current dietary recommendations comprise a high energy (>120% of recommended daily allowances), high fat and high protein diet (40% and 15%, respectively). Since high dietary fat is the main energy source for patients with cystic fibrosis, fat absorption is currently the marker of effective nutrient digestion in cystic fibrosis patients. In addition, providing an appropriate dose and good timing of Pancreatic Enzyme Replacement Therapy (PERT) is of crucial importance to increase lipid digestibility and systemic lipid availability in CF.

In refractory patients who do not respond to Pancreatic Enzyme Replacement Therapy, fecal energy content and fecal fat balance study is the non-invasive gold standard method to assess pancreatic exocrine function by measuring the consequence of reduced fat digestion and absorption. This technique is based on a measurement of triglycerides in feces during a three day collection period and careful determination of fat intake to be able to calculate the fat balance. In daily practice, the appropriate dose of Pancreatic Enzyme Replacement Therapy is determined on clinical ground (symptoms and weight gain) alone, because the fecal fat balance test is unpleasant, unpractical, and cumbersome.

No information is available regarding the acute effect of Pancreatic Enzyme Replacement Therapy on lipid digestion in CF, which is of particular importance in patients who receive continuous night time gastro-intestinal tube feeding. When pancreatic enzymes are given at the beginning of enteral feeding, the duration of enzyme activity, absolute necessity and timing of a second dose, and appropriate dose to improve fat digestion are unknown. Because the current standard technique measures over a 72-hour period, this technique represents a long term fat digestion and absorption capacity and cannot be used to measure acute changes in fat digestibility. Thus, there is no established technique available to measure acute fat digestibility in CF.

Techniques that use carbon-labeled radioactive or stable isotope fatty acids have been described, measuring the labeled $CO_2$ production after ingestion of the labeled fatty acids. These methods have been used in patients with CF to detect fat malabsorption and to monitor the efficacy of Pancreatic Enzyme Replacement Therapy. However these methods have several disadvantages (e.g., the results are a combination of the process of fat digestion and absorption, and are related to metabolism and oxidation of fatty acids to $CO_2$ in the body) and therefore are not used anymore to calculate fat uptake in CF.

The prior art is deficient in techniques for the measurement of protein and/or fat digestibility. The present invention fulfills this longstanding need and desire in the art.

SUMMARY OF THE INVENTION

The present invention is directed to a method for determining reduced protein digestibility in an individual in need of such determination, comprising the step of: administering a meal comprising an isotope labeled protein and a free amino acid tracer to said individual and to a control subject; and measuring the amount of isotope labeled amino acid formed after digestion of said isotope labeled protein and measuring the amount of free amino acid tracer in a biological sample of said individual and said control subject to determine a ratio of isotope labeled amino acid to free amino acid tracer for said individual and for said control subject; wherein a lower ratio of labeled amino acid to free amino acid tracer in said individual compared to the ratio of labeled amino acid to free amino acid tracer from said control subject indicates that said individual has a reduced capacity to digest protein.

The present invention is directed further to a method for obtaining protein digestibility profile in an individual, comprising the step of: administering a meal comprising an isotope labeled protein and a free amino acid tracer to said individual; measuring the amount of isotope labeled amino acid formed after digestion of said isotope labeled protein in a biological sample of said individual and measuring the amount of free amino acid tracer in the biological sample to determine a ratio of isotope labeled amino acid to free amino acid tracer; and repeating said measuring step one or more times to obtain a protein digestibility profile for said individual.

The present invention is directed further still to a kit for determining reduced protein digestibility, comprising: an isotope labeled protein; a free amino acid tracer; and instructions for determining protein digestibility.

In another preferred embodiment, the present invention is directed to a method for determining reduced fat digestibility in an individual in need of such determination, comprising the step of: administering a meal comprising a stable isotope labeled triglyceride and a free fatty acid tracer to said individual and a control subject; and measuring the amount of isotope labeled fatty acid formed after digestion of said isotope labeled triglyceride and measuring the amount of free fatty acid tracer in a biological sample of said individual and said control subject to determine a ratio of isotope labeled fatty acid to free fatty acid tracer for said individual and said control subject; wherein a lower ratio of labeled fatty acid to free fatty acid tracer in said individual compared to the ratio of labeled fatty acid to free fatty acid tracer from said control subject indicates that said individual has a reduced capacity to digest fat.

The present invention is directed further to a method for obtaining fat digestibility profile in an individual, comprising the step of: administering a meal comprising a stable isotope labeled triglyceride and a free fatty acid tracer to said individual; measuring the amount of isotope labeled fatty acid formed after digestion of said isotope labeled triglyceride and measuring the amount of free fatty acid tracer in a biological sample of said individual to determine a ratio of isotope labeled fatty acid to free fatty acid tracer; and repeating said measuring step one or more times to provide a fat digestibility profile for said individual.

The present invention is directed further still to a kit for determining reduced fat digestibility, comprising: an isotope labeled triglyceride; a free fatty acid tracer; and instructions for determining fat digestibility.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
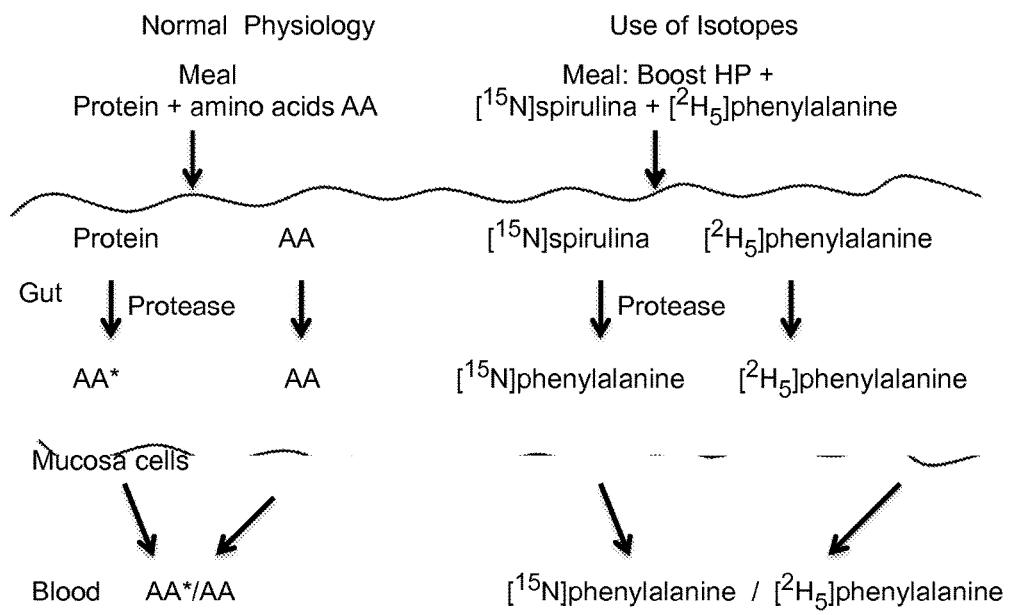
FIGS. 1A-1B show the principle to measure protein digestibility (FIG. 1A) and fat digestibility (FIG. 1B).

Unless otherwise noted, technical terms are used according to conventional usage. Definitions of common scientific technical terms may be found, for example, in Mcgraw-hill Dictionary of Scientific & Technical Terms published by Mcgraw-hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "subject" or "individual" refers to a mammal, preferably a human, who is a recipient of any therapeutic agent or other molecules described herein.

As used herein, the term "enteral administration" refers to route of drug administration that involves absorption of the drug through the gastrointestinal tract.

In one embodiment of the present invention, there is provided a method for determining reduced protein digestibility in an individual in need of such determination, comprising the step of: administering a meal comprising an isotope labeled protein and a free amino acid tracer to said individual and to a control subject; and measuring the amount of isotope labeled amino acid formed after digestion of said isotope labeled protein and measuring the amount of free amino acid tracer in a biological sample of said individual and said control subject to determine a ratio of isotope labeled amino acid to free amino acid tracer for said individual and for said control subject; wherein a lower ratio of labeled amino acid to free amino acid tracer in said individual compared to the ratio of labeled amino acid to free amino acid tracer from said control subject indicates that said individual has a reduced capacity to digest protein. In a non limiting example, the subject has cystic fibrosis. In aspects of this embodiment, representative examples of an isotope labeled protein include but are not limited to $^{15}$N-labeled spirulina protein, $^{15}$N-labeled milk protein, $^{15}$N-labeled soy protein, or $^{15}$N-labeled wheat protein wherein said isotope labeled protein comprises an isotope-labeled amino acid. For example, the isotope-labeled amino acid may be $^{15}$N-labeled amino acid, $^{13}$C-labeled amino acid or $^{2}$H labeled amino acid. Representative examples of labeled amino acid include but are not limited to $^{2}$H-phenylalanine, $^{2}$H-lysine, $^{2}$H-leucine, $^{15}$N-phenylalanine, $^{15}$N-lysine, $^{15}$N-leucine, $^{13}$C-phenylalanine, $^{13}$C-lysine, or $^{13}$C-leucine. In aspects of this embodiment, the free amino acid tracer is $^{2}$H-labeled amino acid, $^{15}$N-labeled amino acid or $^{13}$C-labeled amino acid. For example, the free amino acid tracer may be $^{2}$H-phenylalanine, $^{2}$H-lysine, $^{2}$H-leucine, $^{15}$N-phenylalanine, $^{15}$N-lysine, $^{15}$N-leucine, $^{13}$C-phenylalanine, $^{13}$C-lysine, or $^{13}$C-leucine. In all embodiments, the biological sample is blood or plasma.

Provided herein is kit for determining reduced protein digestibility, comprising: an isotope labeled protein; a free amino acid tracer; and instructions for determining protein digestibility.

In another embodiment of the invention, there is provide a method for obtaining protein digestibility profile in an individual, comprising the step of: administering a meal comprising an isotope labeled protein and a free amino acid tracer to said individual; measuring the amount of isotope labeled amino acid formed after digestion of said isotope labeled protein in a biological sample of said individual and measuring the amount of free amino acid tracer in the biological sample to determine a ratio of isotope labeled amino acid to free amino acid tracer; and repeating said measuring step one or more times to obtain a protein digestibility profile for said individual. In the aspects of this embodiment, said isotope labeled protein is $^{15}$N-labeled spirulina protein, $^{15}$N-labeled milk protein, $^{15}$N-labeled soy protein, or $^{15}$N-labeled wheat protein. The free amino acid tracer is $^{2}$H-phenylalanine, $^{2}$H-lysine, $^{2}$H-leucine, $^{15}$N-phenylalanine, $^{15}$N-lysine, $^{15}$N-leucine, $^{13}$C-phenylalanine, $^{13}$C-lysine, or $^{13}$C-leucine.

In yet another preferred embodiment of the invention, there is a method for determining reduced fat digestibility in an individual in need of such determination, comprising the step of: administering a meal comprising a stable isotope labeled triglyceride and a free fatty acid tracer to said individual and a control subject; and measuring the amount of isotope labeled fatty acid formed after digestion of said isotope labeled triglyceride and measuring the amount of free fatty acid tracer in a biological sample of said individual and said control subject to determine a ratio of isotope labeled fatty acid to free fatty acid tracer for said individual and said control subject; wherein a lower ratio of labeled fatty acid to free fatty acid tracer in said individual compared to the ratio of labeled fatty acid to free fatty acid tracer from said control subject indicates that said individual has a reduced capacity to digest fat. In a non-limiting example, the subject has cystic fibrosis. In aspects of this embodiment, representative examples of stable isotope labeled triglyceride include but not limited to $[1,1,1\text{-}^{13}C_3]$tripalmitin, $[1,1,1\text{-}^{13}C_3]$triolein, $[U\text{—}^{13}C_{16}]$tripalmitin, or $[U\text{—}^{13}C_{18}]$triolein. The isotope labeled fatty acid formed after digestion of said isotope labeled triglyceride may be $[1\text{-}^{13}C]$palmitic acid, $[1\text{-}^{13}C]$oleic acid, $[U\text{—}^{13}C^{16}]$palmitic acid, or $[U\text{—}^{13}C_{18}]$oleic acid. Representative examples of free fatty acid tracer include but not limited to $[2,2\text{-}^{2}H_2]$palmitic acid, $[2,2\text{-}^{2}H_2]$oleic acid, $(7,7,8,8\text{-}D_4)$palmitic acid, $(9,10\text{-}D_4)$ oleic acid. In all embodiments, the biological sample is blood or plasma.

Provided herein is a kit for determining reduced fat digestibility, comprising: an isotope labeled triglyceride; a free fatty acid tracer; and instructions for determining fat digestibility.

In yet another embodiment of the invention, there is a method for obtaining fat digestibility profile in an individual, comprising the step of: administering a meal comprising a stable isotope labeled triglyceride and a free fatty acid tracer to said individual; measuring the amount of isotope labeled fatty acid formed after digestion of said isotope labeled triglyceride and measuring the amount of free fatty acid tracer in a biological sample of said individual to determine a ratio of isotope labeled fatty acid to free fatty acid tracer; and repeating said measuring step one or more times to provide a fat digestibility profile for said individual. In the aspects of this embodiment, said stable isotope labeled triglyceride is $[1,1,1\text{-}^{13}C_3]$tripalmitin, $[1,1,1\text{-}^{13}C_3]$triolein, $[U\text{—}^{13}C_{16}]$tripalmitin, or $[U\text{—}^{13}C_{18}]$triolein. said free fatty acid tracer is $[2,2\text{-}^{2}H_2]$palmitic acid, $[2,2\text{-}^{2}H_2]$oleic acid, $(7,7,8,8\text{-}D_4)$palmitic acid, or $(9,10\text{-}D_4)$oleic acid.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Protein Digestion Study Materials and Methods

Subjects

Nineteen (19) subjects with cystic fibrosis (CF) were studied of which ten were pediatric subjects, age of 10 to 18 years, and admitted to Arkansas Children's Hospital for pulmonary exacerbation. Nine of the CF patients were adults, age of 18 to 35 years at the time of enrollment. Three of the adult patients were admitted to the University of Arkansas for Medical Sciences for pulmonary exacerbation, and 6 were outpatients. All CF subjects had a diagnosis of CF based on universal diagnostic criteria, were clinically stable at enrollment, and were pancreatic insufficient. The CF inpatients were enrolled at the end of their hospital stay with improvement in lung function ($FEV_1$) at the time of enrollment back to baseline values (determined as $FEV_1$ in past 12 months). Exclusion criteria included established diagnosis of diabetes mellitus, unstable metabolic diseases, and chronic respiratory failure with cor pulmonale. In addition, 8 healthy subjects were recruited in the local community and studied as age-matched control subjects to the adult CF patients. Written informed consent was obtained and the study was approved by the Institutional Review Board of the University of Arkansas for Medical Sciences. This trial is registered at ClinicalTrials.gov under as NCT01494909.

Study Design

Figure 2:
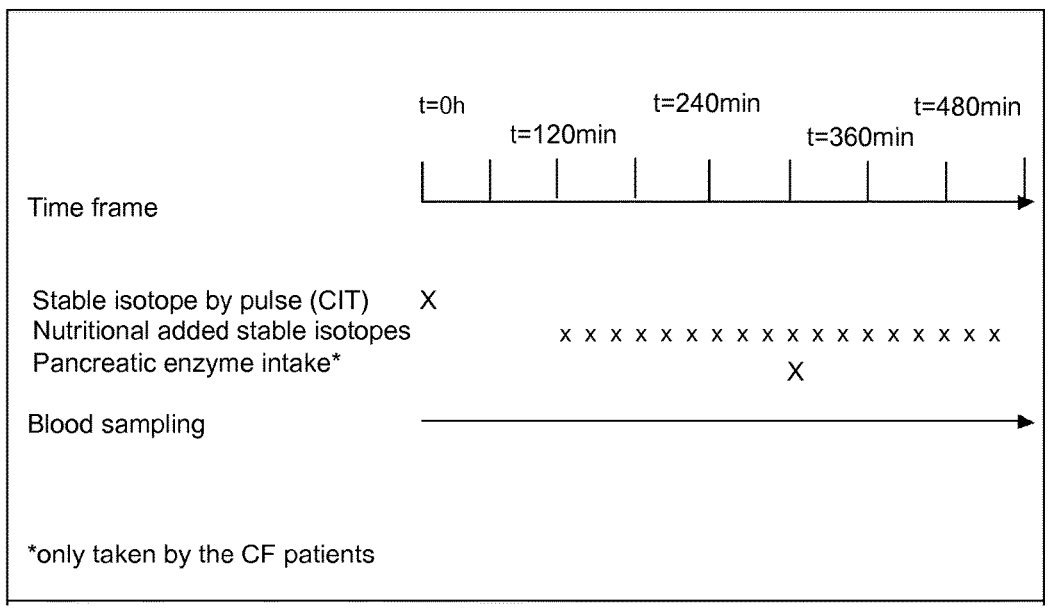
FIG. 2 outlines an overview of the study design for administering nutrition, stable isotopes and pancreatic enzyme intake.

The study day was performed in the patient's hospital room during the last days of antibiotic treatment for a CF exacerbation at Arkansas Children's Hospital (CF children, n=10) or University of Arkansas for Medical Sciences (CF adults, n=3). Moreover, 6 adults with CF and 8 healthy adults were studied at the outpatient clinical research center at University of Arkansas for Medical Sciences. The study day started in the early morning after overnight fasting and lasted for 8 hours. If present, a central-venous port or peripheral line already in place for clinical care was used; otherwise, a catheter was placed in a superficial vein of the lower arm. This line was used for background blood sampling, the bolus infusion of the stable isotope of citrulline (L-[5-$^{13}$C-5,5-$^{2}$H$_2$]-Cit) (Sigma-Aldrich; St. Louis, Mo.) as well as for subsequent blood sampling. Two hours after the IV citrulline bolus, each subject ingested orally or received enterally (when feeding tube was present in CF) a commercially available nutritional supplement according to a sip feeding protocol (each 20 min) during 6 hours. The oral isotopes of $^{15}$N-spirulina and L-[ring-$^2$H$_5$]Phenylalanine (Cambridge Isotopic Laboratories, Andover, Mass.) were added to the nutritional supplement. After 2 hours of sip feeding, one serving of pancreatic enzymes (Creon®, 4000 u lipase/g fat intake) (Abbott; Abbott Park, Ill.) was ingested by the CF subjects. No pancreatic enzymes were taken by the healthy adults. Arterialized-venous blood samples were taken throughout the study for analysis of concentrations and tracer-tracee ratios (TTR) of amino acids. An overview of study design is outlined in FIG. 2.

Composition of the Nutritional Supplement and Pancreatic Enzyme Dose

Figure 1B:
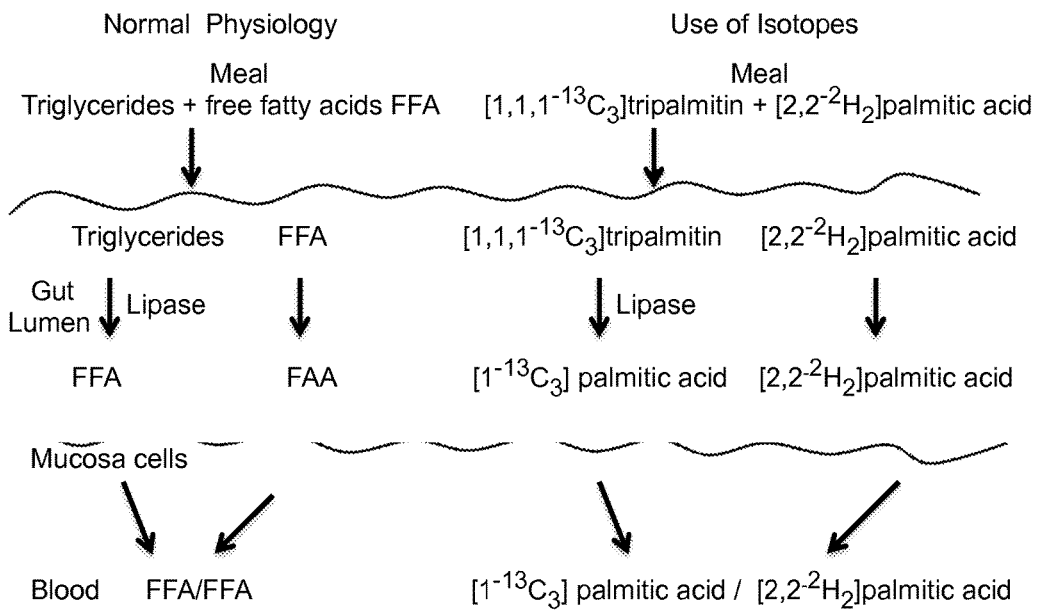

All subjects received a commercially available nutritional supplement, Ensure Plus® (Abbott Nutrition; Abbott Park, Ill.), which is often used in CF care. The subjects ingested the nutritional supplement orally according to a sip feeding protocol (every 20 min) or enterally when a gastrostomy tube was present (CF children, n=3). The dosage of the nutritional supplement for each subject was based on ⅓$^{rd}$ of their total daily protein needs, estimated using Dietary Reference Intakes (DRI) (for composition see Table 1). The stable isotopes $^{15}$N-spirulina protein (63 mg/kg BW Spirulina protein that contains about 1.7 mg L-[$^{15}$N]phenylalanine (PHE)) and L-[ring-$^2$H$_5$]PHE (3.14 mg/kg BW) was added to the nutritional supplement (3.6 g/kg BW Ensure Plus®) to measure protein digestion rate (=ratio [$^{15}$N]PHE to [$^2$H$_5$]PHE in plasma) (for an outline of principle physiology, see FIG. 1). The nutritional supplement was mixed with the oral stable isotopes and divided into equal portions and stored in the refrigerator before use. A sample of the supplement was stored for composition and PHE isotope ratio analysis.

Pancreatic enzyme (Creon®) intake in CF took place at 2 h into feeding, and the dose was based on the fat content of the meal (4000 u lipase/g fat) (Table 1). The pancreatic enzymes for the children and adults with CF were obtained from the Arkansas Children Hospital and University of Arkansas for Medical Sciences pharmacy, respectively.

TABLE 1

Nutrition, pancreatic enzyme and oral isotope dose used in children and adults with Cystic Fibrosis and healthy adults

|  |  | Healthy adults | CF adults | CF children |
|---|---|---|---|---|
| Ensure plus | ml | 260.1 ± 36.9 | 224.3 ± 37.3 | 170.8 ± 39.4 |
| Creon 12000 | U | 0 | 3.56 ± 0.53 | 2.5 ± 0.53 |
| Creon 6000 | U | 0 | 0.11 ± 0.33 | 0.50 ± 0.53 |
| $^{15}$N-Spirulina | mg | 4572.8 ± 648.5 | 3943.3 ± 656.2 | 3003.0 ± 693.1 |
| $^2$H$_5$-Phenylalanine | mg | 228.6 ± 32.5 | 197.2 ± 32.8 | 150.1 ± 34.6 |

Values are means ± SEM

Anthropometric Data and Body Composition

In the early morning of the study day, body weight and height were measured in all subjects by a digital beam scale and stadiometer, respectively. BMI was calculated by dividing body weight by squared height and expressed in kg/m$^2$ for the adults. Height, weight, and BMI percentiles of the CF children were calculated in accordance with the CF consensus report (1). Whole-body fat mass (FM) and fat-free mass (FFM) were obtained by dual-energy X-ray absorptiometry (DXA) (Hologic QDR 4500/Version 12.7.3.1; Bedford, Mass.) when the subjects were in supine position. The DXA procedure was conducted in the outpatient research setting on the study day, or obtained during hospital stay in case of hospital admission.

The anthropometric and body composition data were standardized for height to obtain BMI, fat-free mass index (FFMI), and fat mass index (FMI). FFMI and FMI were expressed as percentage of published reference data Nutritional failure was defined as FFMI<5th percentile in accordance to previous studies in CF and/or BMI<10th percentile (age≤20 years) or BMI<18 kg/m2 (age 21 years and older) using the Cystic Fibrosis Foundation selected BMI cut-off point.

Lung Function

Forced expiratory volume in 1 second (FEV$_1$) and forced vital capacity (FVC) were measured by spirometry (nSpire Health; Longmont, Colo.) in all CF participants and reference equations were used to calculate FEV$_1$ and FVC % predicted values.

Biochemical Analysis

Blood samples were put in Li-heparinized tubes, immediately put on ice and instantly frozen and stored at −80° C. until further analyses. Samples of the nutritional supplement were hydrolyzed in 6N HCl solution for 24 h at 110° C. All samples obtained were analyzed in a batch. Analysis for enrichment and concentrations was done by LC-ESI-MS (QTrap 5500MS) (AB Sciex; Foster City, Calif.) with ExpressHT Ultra LC (Eksigent AB Sciex; Foster City, Calif.) after derivatization with 9-fluorenylmethoxycarbonyl (Fmoc). FMoc-PHE and Fmoc-CIT were fragmented to obtain specific and high sensitivity fragments.

Calculations for Protein Digestibility and Whole Body Citrulline Production

Stable isotope of $^{15}$N-spirulina protein and $^2$H$_5$-phenylalanine was added to the nutritional supplement (FIG. 1A) in which $^2$H$_5$-phenylalanine does not need digestion before absorption (digestibility=100%). Protein digestibility is calculated by measuring the ratio [$^{15}$N]PHE to [$^2$H$_5$]PHE in plasma and the nutrition.

Protein digestibility was calculated by dividing the plasma [$^{15}$N]PHE to [$^2$H$_5$]PHE ratio by the [$^{15}$N]PHE to [$^2$H$_5$]PHE ratio in the nutritional supplement. Protein digestion rate during feeding was calculated as the average value at 200 min to 240 min into the study (=80-120 min after start of sip feeding). Highest plateau value of protein digestion rate after intake of pancreatic enzymes was calculated as the average value at 340 min to 400 min into the study (=100-160 min after intake of pancreatic enzymes in CF).

To assess whole-body citrulline production in the postabsorptive state with a pulse of citrulline isotope, the program SAAM II (Version 2.2) (The Epsilon Group; Charlottesville, Va.) was used to calculate the k values and pool sizes in a two compartmental model. The k values were converted to whole-body rate of appearance (WbRa) or intracellular production as described (2). The compartmental modeling estimates the parameters to calculate WbRa and intracellular production rates in relation to the actual intracellular precursor pool enrichment. These rates are higher than when estimated with primed-constant infusion production, and in that case, the precursor pool enrichment in arterial plasma is used as a proxy of intracellular enrichment, which is higher than the intracellular enrichment as the production takes place intracellularly.

Statistical Analysis

Results are expressed as mean±standard error (SE). Data failing the normality or equal variance test were log-transformed where appropriate. One-way ANOVA was used to determine differences between the children and adults with CF and the healthy subjects, and Newman-Keuls was used as post hoc analysis. Unpaired Student's t test was used to determine differences in clinical changes between the children and adults with CF group, and in the CF group with and without nutritional failure. The level of significance was set at p<0.05. The statistical package within Graphpad Prism (Version 6.01) and SPSS (Version 20) was used for data analysis.

Example 2

Protein Digestion Study Results

The group consisted of 10 children with CF (age: 14.9±0.2 y), 9 adults with CF (age: 28.6±0.8 y), and 8 healthy adults (age: 29.2±1.2 y) (Table 2), Age of the CF adults was not different from the healthy adults. The homozygous DF 508 gene was present in 90% of the children and in 25% of the adults with CF.

The patients with CF were characterized by mild to severe airflow obstruction. Mean $FEV_1$ tended to be lower (P=0.08) and FVC was significantly (P<0.05) lower in the CF adults than in the CF children. The CF adult group was characterized by reduced values for FFMI (as percentage of control values: P<0.05), but no difference in FFM was found between the children and adults with CF. Mean BMI (in $kg/m^2$) was not different between the adults with CF and the healthy subjects. The mean BMI of the CF children was at the 46 percentile indicating lower than the CF recommended BMI of 50%. Three adults (33%) and 3 children with CF (30%) were characterized by nutritional failure.

TABLE 2

General characteristics of the children and adults with Cystic Fibrosis and healthy adults

|  |  | Healthy adults | CF adults | P | CF children | P |
|---|---|---|---|---|---|---|
| Gender | m/f | 4/4 | 5/4 |  | 6/4 |  |
| Age | Y | 29.2 ± 1.2 | 28.6 ± 0.8 |  | 14.9 ± 0.2 | <0.001[a] |
| BMI | $Kg/m^2$ | 23.5 ± 0.4 | 21.6 ± 0.5 |  | | |
|  | Percentile |  |  |  | 46.4 ± 3.0 | |
| FFMI | % norm | 102.3 ± 1.6 | 90.7 ± 1.5 | 0.05 | 92.8 ± 1.1 | |
| FMI | % norm | 113.0 ± 17.3 | 99.4 ± 18.1 |  | 96.8 ± 10.0 | |
| Nutritional failure | y/n | 0/8 | 3/6 |  | 3/7 | |
| $FEV_1$ | % pred |  | 63.9 ± 3.3 |  | 81.6 ± 1.3 | 0.08[a] |
| FVC | % pred |  | 76.6 ± 3.6 |  | 98.0 ± 1.6 | 0.04[a] |
| CF genotype |  |  | DF508/DF508, DF508/G 542x, unknown: n = 2, DF508/2184delA, DF508/G1244: n = 1 |  | DF508/DF50 8: n = 9; DF508/1717- 1GtoA: n = 1 | |

Figure 3A:
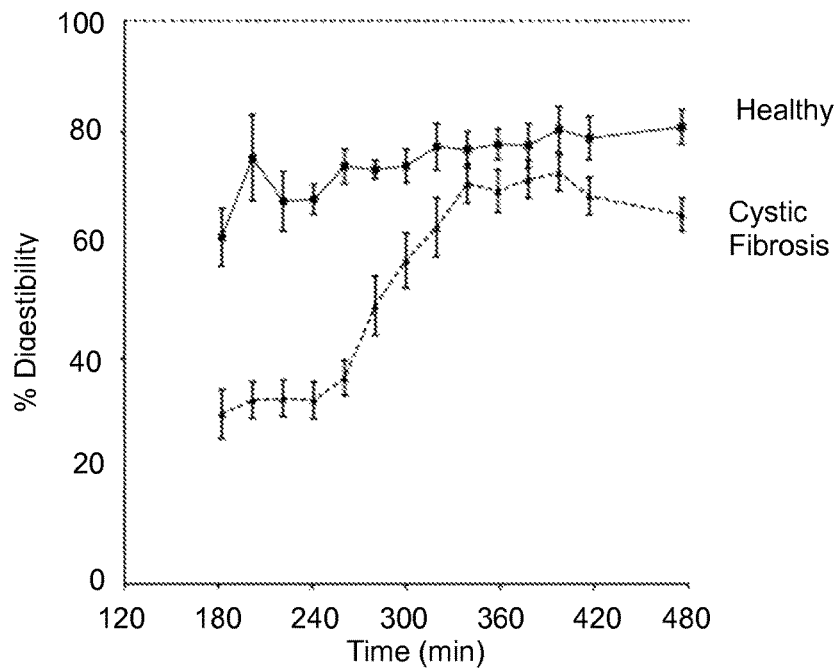
FIGS. 3A-3B show the response in protein digestibility during feeding and after intake of pancreatic enzymes (only in CF) in the whole CF group (dashed line) and healthy adult group (solid line) (FIG. 3A), and in the healthy group (solid line) and after stratification of the whole CF group into adults (dashed line) and children (dotted line) (FIG. 3B).

Values are means ± SEM. CF: Cystic Fibrosis, BMI: Body mass index, FFMI: Fat-free mass index, $FEV_1$: forced expiratory volume in one second, FMI: fat mass index, FVC: forced vital capacity. The P value represents a comparison with Healthy adults.
[a]P value represents a comparison with CF adults Protein Digestibility In healthy young adults, protein digestibility was about 80% in line with reported rates of spirulina protein (FIG. 3). The average protein digestibility during feeding and before the pancreatic enzyme intake (t=200-240 min) was significantly lower in the total CF group as compared to the healthy subjects (p<0.001) which corresponded to 46.5% of the healthy subjects (FIG. 3A). After pancreatic enzyme intake protein digestibility increased in CF and reached its maximal value at 344 min (=104 min) of 90.3% of the healthy subjects and a plateau in digestibility occurred for approximately 80 minutes.

Figure 3B:
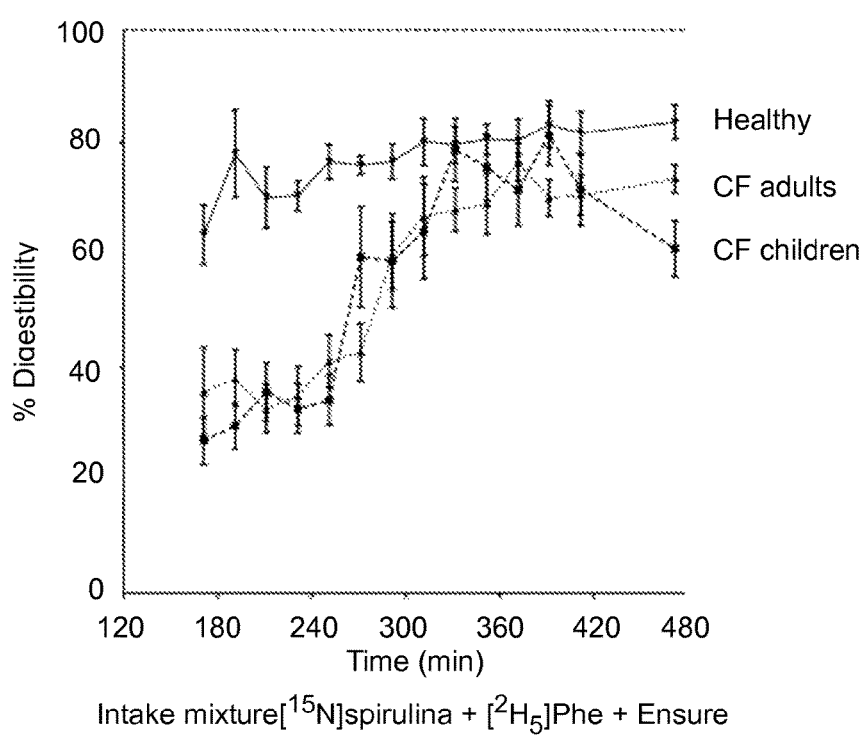

Stratification of the CF group into adults and children showed comparable values for protein digestibility during feeding (as % of the healthy subjects) in both groups (44.7% vs. 48.3%, ns) and a similar kinetic response to pancreatic enzyme intake (FIG. 3B). Between 340 and 420 min, protein digestibility reached average (plateau) values of 93.4% vs. 87.4% of the healthy subjects in the CF children vs. CF adults, respectively. No difference was found in average protein digestibility during feeding or after pancreatic enzyme intake between CF patients with and without the homozygous DF 508 gene, or between CF patients with or without nutritional failure. Furthermore, no significant relationship was found with lung function in the CF group.

Whole-Body Rate of Appearance and Production Rate of Citrulline

Figure 4A:
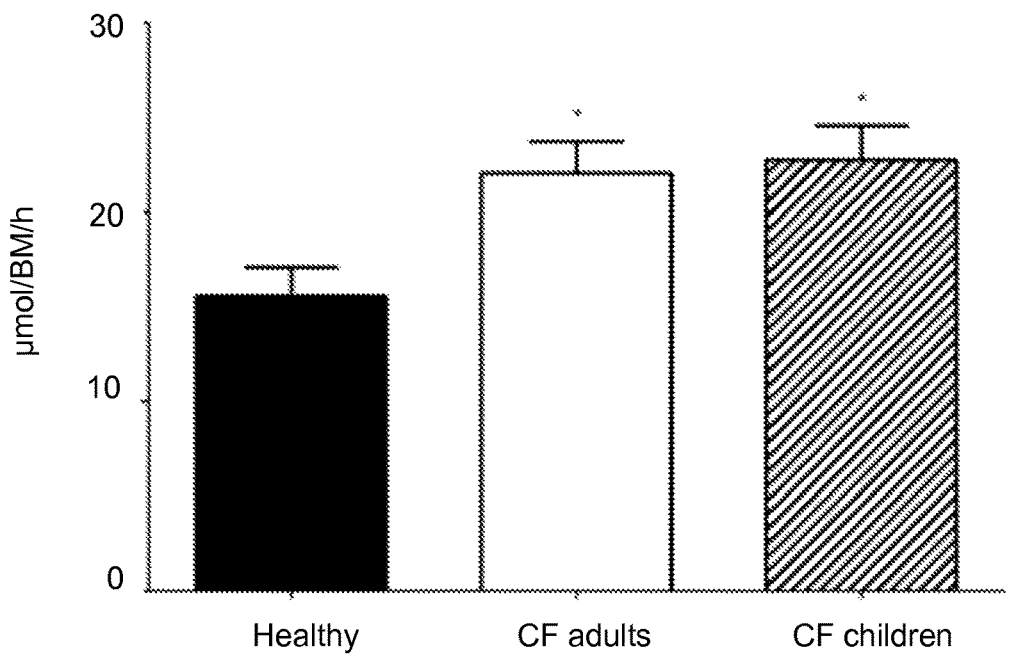
FIGS. 4A-4D shows postabsorptive whole body rate of appearance (WbRa, FIGS. 4A, 4C) and production rate (FIGS. 4B, 4D) of citrulline in the healthy adult group (solid bar) and after stratification of the whole CF group into adults (open bar) and children (cross striped bar), and after stratification of the CF group into nutritional failure (NF, vertical striped bar) and no nutritional failure (no NF, horizontal striped bar). Mean values±SE are shown. Significance of difference as compared to the healthy group (*: $P<0.05$, **: $P<0.01$) and as compared to the CF group with no nutritional failure (#: $P<0.05$).
Figure 4B:
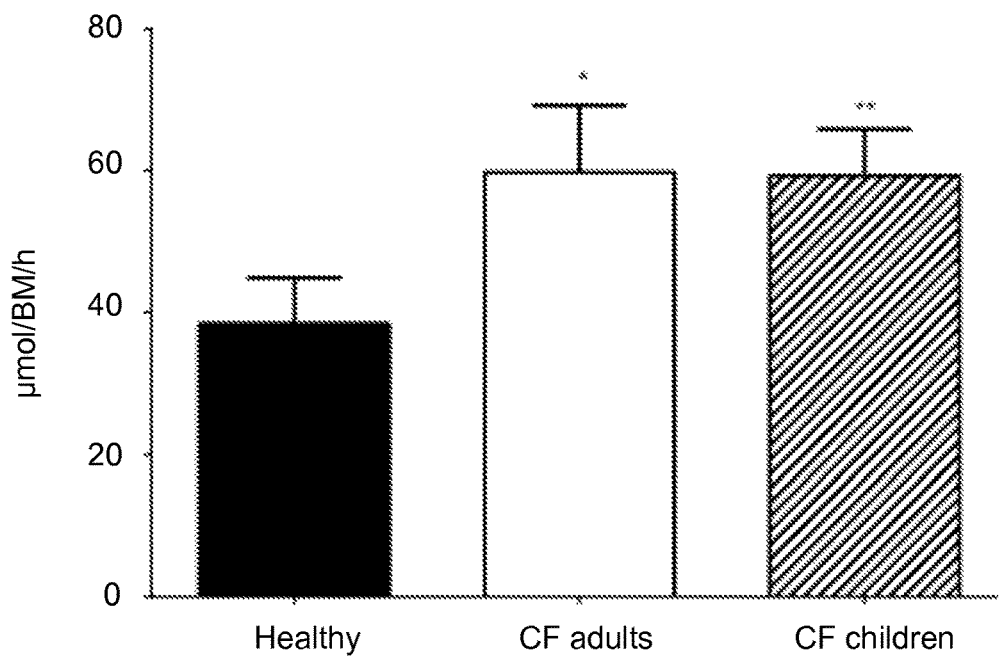
Figure 4C:
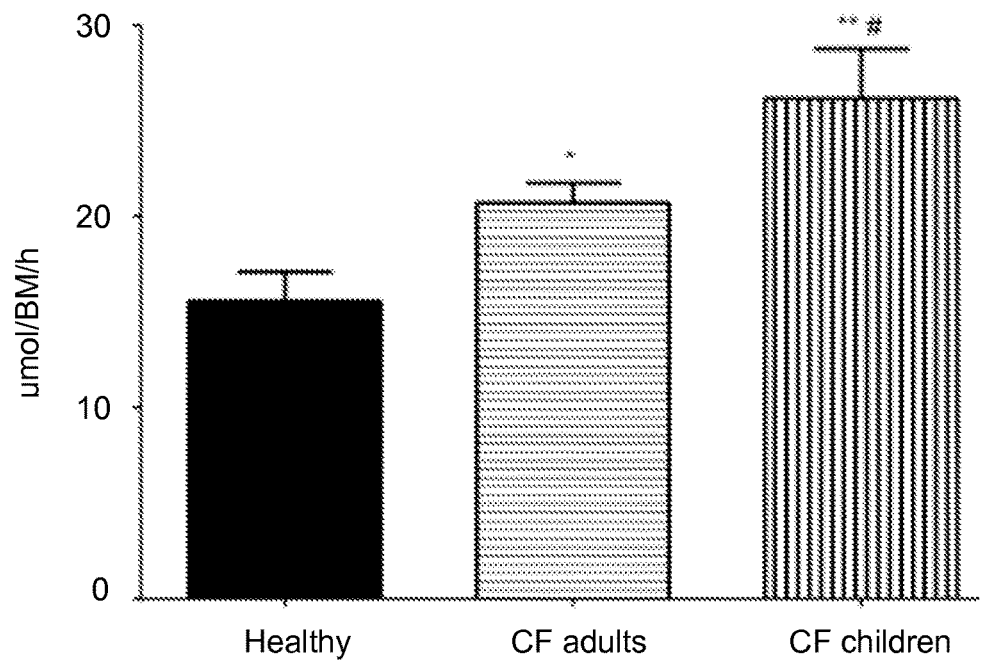
Figure 4D:
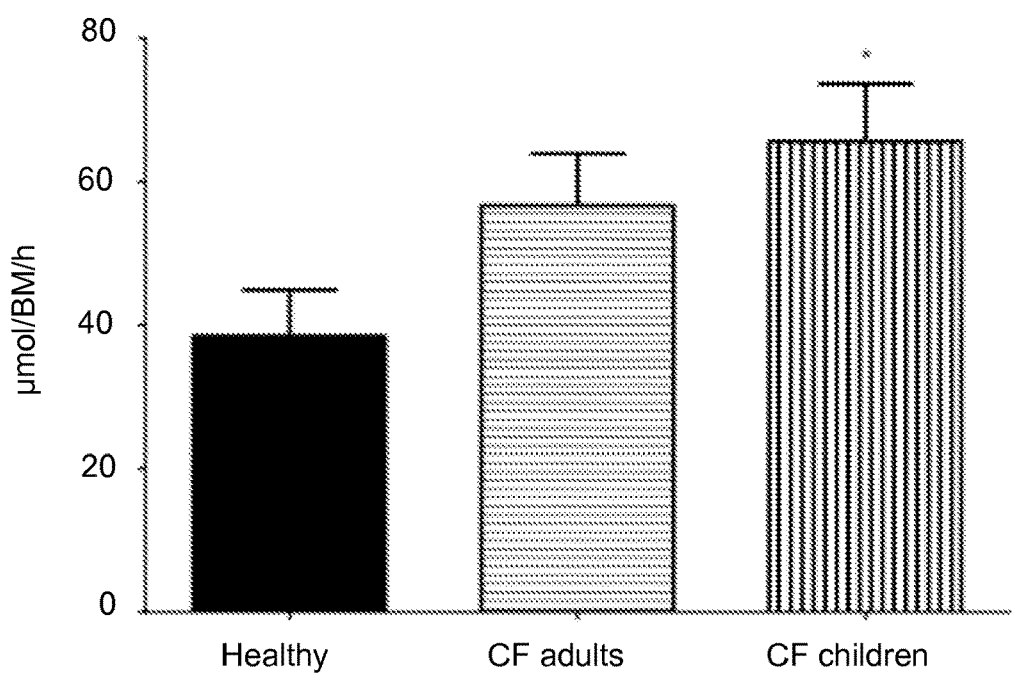

Whole-body citrulline rate of appearance (FIGS. 4A, 4C) and production rate (FIGS. 4B, 4D) were significantly higher in the CF patients as compared to the healthy subjects in the postabsorptive state (p<0.05). However, no difference was present between the adults and children with CF. Plasma citrulline concentration was not significantly different in CF as compared to the healthy group (41±4 µmol/L vs. 33±2 µmol/L; p=0.1), Significant higher values were found for whole-body citrulline rate of appearance in the CF patients with nutritional failure as compared to those without nutritional failure (P<0.05). Whole-body citrulline rate of appearance and production rate were not related to lung function or protein digestibility during feeding (data not shown).

Example 3

Fat Digestion Study Materials and Methods

Subjects

The study population consisted of 10 pediatric subjects with CF, ages 10-18 years at the time of enrollment and admitted to Arkansas Children's Hospital for antibiotic treatment of a pulmonary exacerbation. Furthermore, 9 adults with CF, age of 18 to 35 years at the time of enrollment were studied. Three of them were admitted to University of Arkansas for Medical Sciences for antibiotic treatment of a pulmonary exacerbation, and 6 were stable outpatients. The CF subjects were enrolled with a diagnosis of CF based on universal diagnostic criteria, abnormal lipid digestion requiring pancreatic enzyme replacement therapy, and improvement in lung function ($FEV_1$) at the time of enrollment back to baseline values (determined as $FEV_1$ in past 12 months). Exclusion criteria included established diagnosis of diabetes mellitus, unstable metabolic diseases, and chronic respiratory failure with cor pulmonale). Written informed consent was obtained and the study was approved by the Institutional Review Board. This trial is registered at ClinicalTrials.gov under as NCT01494909.

Composition of the Nutritional Supplement

All subjects received a nutritional supplement, Ensure plus. The subjects ingested the nutritional supplement orally according to a sip feeding protocol (every 20 min) or enterally (when feeding tube is present in CF subjects (n=3 pediatric CF)). The dosage of the nutritional supplement for each subject was based on $\frac{1}{3}^{rd}$ of their total daily protein needs, estimated using Dietary Reference Intakes (DRI). The stable isotopes of $[1,1,1-^{13}C_3]$tripalmitin and $[2,2-H_2]$palmitic acid were added to measure fat digestion rate (=ratio $[1-^{13}C]$palmitic acid to $[2,2-^2H_2]$palmitic acid). The nutritional supplement was mixed with the oral stable isotopes and divided into equal portions and stored in the refrigerator before use. Pancreatic enzyme (Creon®) intake in CF took place at 2 h into feeding and the dose was based on the fat content of the meal (4000 u/g fat intake). No pancreatic enzymes were taken by the healthy adults. Pancreatic enzymes were obtained from ACH and UAMS pharmacy.

Anthropometric Data and Body Composition

Body weight and height were measured by a digital beam scale and stadiometer, respectively. BMI was calculated by dividing body weight by squared height. Height, weight and BMI percentiles of the CF subjects were calculated in accordance with the CF consensus report (1). Whole body fat mass (FM) and fat-free mass (FFM) were obtained in the patients with CF by dual-energy X-ray absorptiometry (DXA) (Hologic QDR 4500/Version 12.7.3.1 Bedford, Mass.) when the patients were in supine position. The anthropometric and body composition data were standardized for height to obtain BMI, FFMI, and FMI and expressed as percentage of published reference data. Body composition was determined in the whole body as well as in the arms, legs, and trunk. The DXA procedure was done once during hospital stay or the data were copied from subject's file when DXA was performed in the preceding month of the study as part of CF care. Nutritional failure was defined as $FFMI<5^{th}$ percentile in accordance to previous studies in CF and/or $BMI<10^{th}$ percentile (age≤20 years) or BMI<18 $kg/m^2$ (age 21 and older) the Cystic Fibrosis Foundation selected BMI cut-off point (3).

Lung Function

Forced expiratory volume in 1 second ($FEV_1$) and forced vital capacity (FVC) was measured by spirometry (nSpire Health, Longmont, Colo.) in all participants and reference equations (2) were used to calculate $FEV_1$ and FVC % predicted values.

Study Protocol

The study days were performed in the patient's hospital room during the last days of 2 weeks of antibiotic treatment for a CF exacerbation at Arkansas Children's Hospital (CF children) or UAMS (CF adults). The adult CF patients and the healthy adults were studied at the Center translational research at UAMS. The study day started in the early morning after overnight fasting and lasted for approx. 8 hours. Body weight and height were measured and a catheter was placed in a superficial vein of the lower arm or the central-venous port for blood sampling, or a peripheral line already in place for clinical care was used. After 2 hours in the postabsorptive state, each subject ingested orally or received enterally (when feeding tube was present in CF subject) a commercially available nutritional supplement that generally is used in CF care (Ensure plus) according to a sip feeding protocol (each 20 min) during 6 hours. To the nutritional supplement, the oral isotopes of $[1,1,1-^{13}C_3]$ tripalmitin (1 µmol/kg BW/h), and $[2,2-H_2]$palmitic acid (3 µmol/kg BW/h) were added. After 2 hours of feeding, one serving of pancreatic enzymes (Creon®, 4000 u/g fat intake) was ingested by the CF subjects. No pancreatic enzymes were taken by the healthy adults. Blood was sampled once for analysis of the natural enrichment of amino acids. Arterialized-venous blood samples were taken throughout the study for analysis of concentrations and tracer-tracee ratios (TTR) of amino acids.

Biochemical Analysis

Arterialized-venous blood samples were put in Li-heparinized or EDTA tubes (Becton Dickinson Vacutainer system, Franklin Lakes, N.J.) and immediately put on ice to minimize enzymatic reactions. The blood was centrifuged and put in 50% sulfosalicyl acid matrices to deproteinize the plasma, and then instantly frozen and stored at −80° C. until further analyses. All samples obtained were analyzed in a batch according to routine measurements (4, 5).

Calculations $[1,1,1-^{13}C_3]$tripalmitin and $[2,2-^2H_2]$palmitic acid were added (FIG. 1B) to the meal and the ratio between the appearance of free fatty acids for digestion of triglycerides is measured when 100% of triglycerides are digested. The ratio between $[1-^{13}C]$palmitic acid/$[2,2-^2H_2]$palmitic acid represents the percentage digestion of triglycerides by lipase from the pancreas.

Statistical Analysis

Results are expressed as mean±standard error (SE). The level of significance was set at p<0.05. The statistical package within Graphpad Prism (Version 5.04), and SPSS (version 20) was used for data analysis.

Example 4

Fat Digestion Study Results

The group consisted of 10 children with CF (mean age: 14.9±0.2 y), 9 adults with CF (mean age: 28.6±0.8 y), and 8 healthy adults (29.2±1.2 y) (Table 3). Age of the CF adults was not different from the healthy adults. The patients had mild to severe airflow obstruction and were characterized on average by reduced values for FFM and FM. $FEV_1$ and FVC was significantly lower in the CF adults than in the CF children (P<0.05). Three of the adults and 3 of the children with CF had nutritional failure based on BMI<10 percentile and/or FFMI<$5^{th}$ percentile.

Figure 5A:
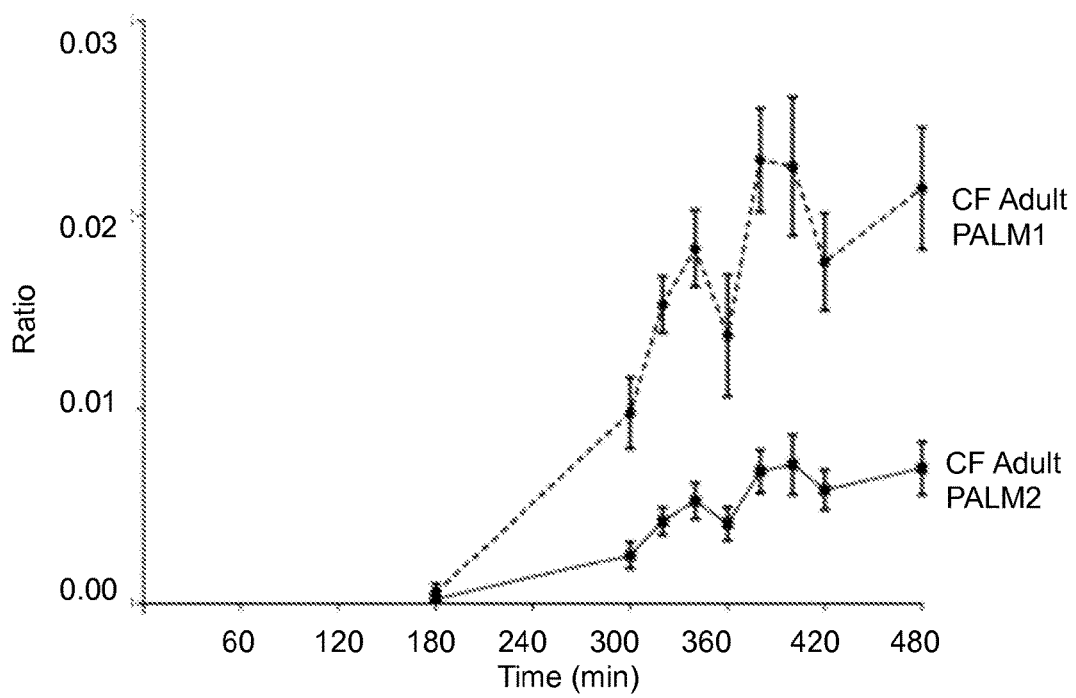
FIGS. 5A-5B show the tracer tracee ratio response of Palmitate mass 2 (dashed line) and mass 1 (dotted line) in the CF adult (FIG. 5A) and CF children (FIG. 5B).
Figure 5B:
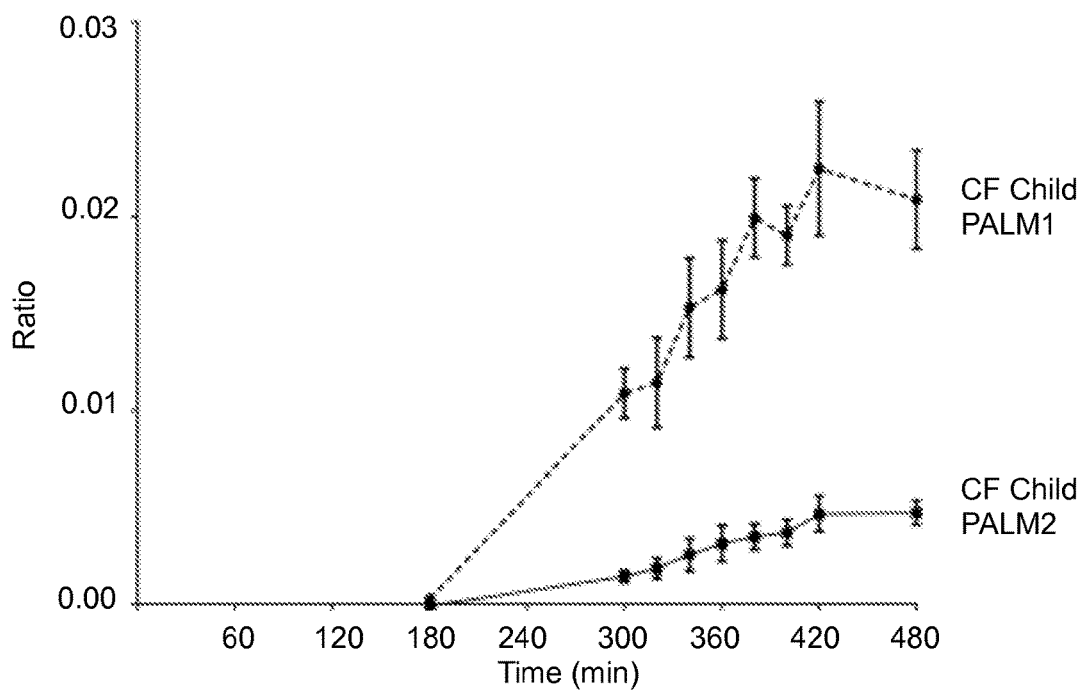

Compared to healthy subjects, fat digestion rate during feeding (at 240 min into the study) were on average 57% and 49% of normal in the whole CF group (FIG. 5A-5B). Intake of the pancreatic enzymes gradually increased fat digestion to 68% of normal at 4 h after the enzyme intake.

Figure 6A:
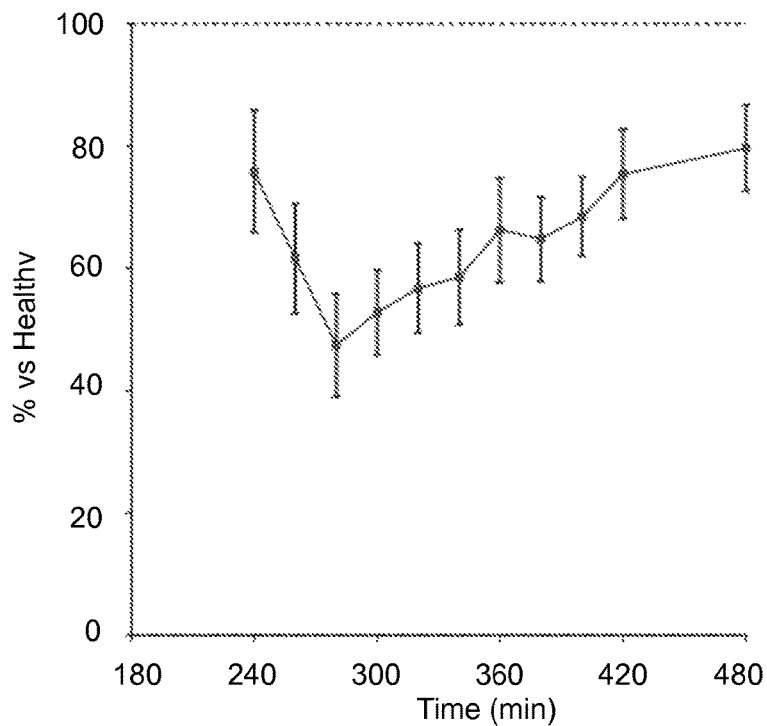
FIGS. 6A-6B show the response in fat digestion rate in CF group (FIG. 6A), compared to the fat digestion rate in the healthy control group (dashed line; set at 100%) and after stratification of the whole CF group into adults (dashed line) and children (dotted line), during feeding and after intake of pancreatic enzymes (FIG. 6B; only in CF).
Figure 6B:
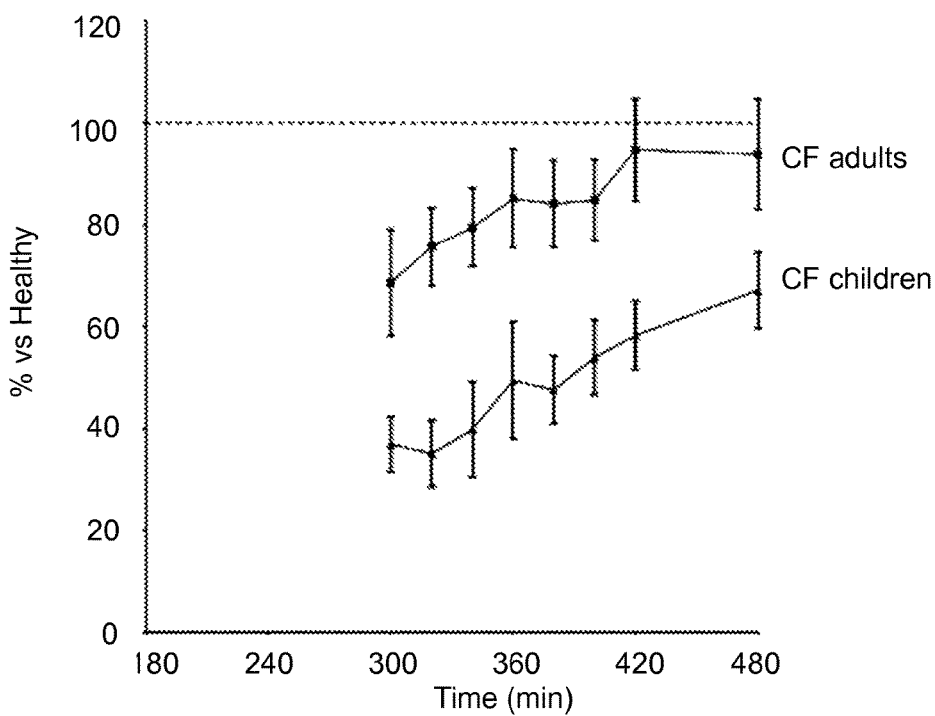

Stratification of the CF group in children (n=10, $FEV_1$: 82±1% pred) and adults (n=9, $FEV_1$:64±3% pred.) showed a lower fat digestion rate (FIG. 6A) in CF children during feeding (43 vs. 68% resp., P<0.05) at 240 min into the study. For the fat digestion rate, there was a significant group (P<0.001) and time effect (P<0.01) but no interaction, indicating that the increase in the fat digestion rate after pancreatic enzyme intake (FIG. 6B) was comparable in children and adults with CF but the absolute fat digestion rate remained lower in the CF children even at 4 hours after pancreatic enzyme intake (67 vs. 94% resp., P<0.05).

protein digestibility after pancreatic enzyme intake was present in children and adults with CF.

Approaches to Circumvent the Impaired Protein Digestibility in CF

There are several ways to circumvent the reduced protein digestibility in CF patients while they are on pancreatic enzyme replacement therapy, i.e., adjusting the type of protein intake into more slowly digested proteins, intake of hydrolyzed proteins or free dietary amino acids, changing the timing of pancreatic enzyme intake, and/or by modifying the dose/composition (lipase, protease, amylase) of the pancreatic enzyme capsules. These results indicate that when meals are consumed consisting of proteins that are slowly digested (e.g., casein protein), which mimics the sip feeding protocol used herein, it takes nearly 2 hours for the enzyme activity to achieve a maximal effect in CF patients.

The normalization of protein digestibility that occurred after pancreatic enzyme intake in the studied CF patients suggests that the amount of protease in the pancreatic enzymes is sufficient. However, normalization of protein digestibility was severely delayed as it took nearly 2 hours before protein digestibility was normalized, suggesting that the pancreatic enzyme capsules need to be modified during

TABLE 3

General characteristics of the children and adults with CF and the healthy controls

|  |  | Healthy controls | CF adults | CF children |
|---|---|---|---|---|
| Gender | m/f | 4/4 | 5/4 | 6/4 |
| Age | y | 29.2 ± 1.2 | 28.6 ± 0.8 | 14.9 ± 0.2 |
| BMI | Kg/m² | 23.5 ± 0.4 | 21.6 ± 0.5 | 46.4 ± 3.0 |
|  | Percentile |  |  |  |
| FFMI | % norm | 102.3 ± 1.6 | 90.7 ± 1.5 | 92.8 ± 1.1 |
| Nutritional failure | y/n | 0/8 | 3/6 | 3/7 |
| $FEV_1$ | % pred |  | 63.9 ± 3.3 | 81.6 ± 1.3 |
| FVC | % pred |  | 76.6 ± 3.6 | 98.0 ± 1.6 |
| CF genotype |  |  | DF508/DF508: n = 2; DF508/G542x: n = 2; DF508/2184delA, DF508/G1244: n = 1, unknown: n = 2 | DF508/DF508: n = 9; DF508/1717-1G TO A: n = 1 |

Values are means ± SEM.
CF: Cystic Fibrosis,
BMI: Body mass index,
FFMI: Fat-free mass index,
$FEV_1$: forced expiratory volume in one second,
FVC: forced vital capacity Discussion
Protein Digestion Study
Impaired Protein Digestibility in CF During Feeding and Response to Pancreatic Enzyme Intake In the present study, sip feeds were used as a model that reflects supplemental enteral feeding by gastrostomy tube as often used to improve the nutritional status of undernourished CF patients. Tube feeding is administered mostly at night at continuous infusion over 6 to 12 hours and pancreatic enzymes are given at the start of the feeding. The observed protein digestibility during feeding of 47% of normal in CF indicates a severe reduction of protein digestibility that was comparable in adults and children with CF. The dose of pancreatic enzymes was determined on an individual basis taking the fat content and rate of administration of the sip feeding into consideration. It was observed that 100 min were needed after intake of the pancreatic enzymes before protein digestibility reached its maximal value of 90% of normal in CF. A comparable response in continuous feeding to make the enzymes more quickly available and active. Pancreatic enzyme products are labeled according to the amount of lipase they contain. All products also contain protease and amylase, but the labeled and actual amounts of these two enzymes may differ from product to product even when labeled lipase amounts are the same. The data suggests that the pancreatic enzyme products need to work faster during meal intake and that the labeling of the products should also contain the protease activity. For pancreatic enzymes to be effective proteases, it is crucial that they are available when protein in the food reaches the proximal small intestine, which is the place where amino acid uptake mainly takes place. These results indicate that a fast response is essential for the proteases, and therefore the capsules need to be opened to release the proteases in the last part of the duodenum when pH is less acidic, while for the lipases a much slower response is needed as they are irreversibly inactivated at pH 4.0 or lower. The dose and timing of administered pancreatic enzymes in CF should therefore be based on multiple factors like the composition of the diet (amount fat/protein) in order to improve both fat and protein digestibility simultaneously and on factors like gastric acid secretion, pH at different levels of the small and large intestine, patterns of gastric emptying, and bile acid composition and concentration.

Whole-Body Citrulline Production as Measure of Gut Function

In the present study, plasma citrulline concentration was elevated in the CF as compared to the healthy subjects. Therefore, both in CF patients at the end of hospitalization for an acute exacerbation as in stable CF outpatients, gut mucosal function seem to be unaffected. Citrulline is an amino acid released almost exclusively from the small bowel enterocyte mucosal mass as it is not a protein component and as such not incorporated in enteral food or endogenous proteins. In the present study, whole-body citrulline rate of appearance and production rate were also elevated in CF but not related to protein digestion rate during feeding or with the average protein digestion rate obtained after pancreatic enzyme intake in CF. No association was found between whole-body citrulline rate of appearance or production and lung function or age in CF.

However, to measure overall digestibility of meals with proteins, some or all proteins should be labeled with $^{15}N$. Isotope ratio measurements are necessary to be able to calculate the protein digestion rate and these analytical techniques can be easily implemented on available GC-MS or LC-MS machines in the clinic. As the stable isotope-based method measures protein digestibility, no information on amino acid absorption was obtained. As the elevated whole-body citrulline production indirectly indicates that mucosa function is normal in CF, a direct measurement of amino acid absorption could be made by using marker amino acids that are not metabolized in the body (e.g., labeled amino acid analogues), assuming that the marker absorption rates are representative for the amino acid absorption rate in general. Furthermore, in order to test this method, CF patients were studied during continuous (sip) feeding as it closely reflects the situation present in patients with a gastrostomy tube during overnight feeding. In conclusion, protein digestibility during continuous feeding as measured by this novel and easy-to-use stable isotope technique is severely compromised in patients with CF and normalization is possible but delayed after pancreatic enzyme intake. Gut (mucosa) function as measured by whole-body citrulline production is not affected in CF.

Fat Digestion Study

Maldigestion of fat is likely if an individual ingesting 100 g of fat per day excretes more than 7 g of fat in a 24-hour period. In the present study sip feeds were used to reflect supplemental enteral feeding by gastrostomy tube (GT) as this is often used to improve the nutritional status of undernourished CF patients. GT feeding is administered mostly at night at continuous infusion over 6-12 hours. The dose of PERT is worked out on an individual basis taking the type, fat content, and rate of administration of the feeding into consideration. In practice, a starting dose of one to two capsules of the patient's usual enzyme preparation is given at the start and at the end of the feeding. The dose is then titrated against symptoms rather than the fat content of the feed. If bolus feeds are being given or the feeding is being infused over a short period of time, larger enzyme doses may be required due to the faster rate of fat infusion.

The following references are relied on herein.
1. Borowitz D et al. J Pediatr Gastroenterol Nutr 2002; 35:246-59.
2. Wolfe et al., Isotope Tracers in Metabolic Research: Principles and Practice of Kinetic Analysis. New York: Wiley, New York, 2005.
3. Mille C E et al. Clin Chest Med 2007; 28:319-30.
4. Andersen D H et al. Am. J. Dis. Child. 1945; 69:221.
5. Lavik P S et al. Pediatrics 1952; 10:667-76.

What is claimed is:

1. A method for determining reduced fat digestibility in an individual in need of such determination, comprising the steps of:
    orally administering a meal comprising a $[^{13}C]$-labeled triglyceride and a $[^{2}H]$-labeled free fatty acid tracer to said individual and a control subject; and
    measuring the amount of $[^{13}C]$-labeled fatty acid formed after digestion of said $[^{13}C]$-labeled triglyceride and measuring the amount of $[^{2}H]$-labeled free fatty acid tracer in a biological sample of said individual and said control subject to determine a ratio of $[^{13}C]$-labeled fatty acid to $[^{2}H]$-labeled free fatty acid tracer for said individual and said control subject; wherein a lower ratio of $[^{13}C]$-labeled fatty acid to $[^{2}H]$-labeled free fatty acid tracer in said individual compared to the ratio of $[^{13}C]$-labeled fatty acid to $[^{2}H]$-labeled free fatty acid tracer from said control subject indicates that said individual has a reduced capacity to digest fat.

2. The method of claim 1, wherein said $[^{2}H]$-labeled free fatty acid tracer is $[2,2-^{2}H_{2}]$-palmitic acid, $[2,2-^{2}H_{2}]$-oleic acid, or $(7,7,8,8-D_{4})$palmitic acid.

3. The method of claim 1, wherein said $[^{13}C]$-labeled triglyceride is $[1,1,1-^{13}C_{3}]$-tripalmitin, $[1,1,1-^{13}C_{3}]$-triolein, $[U-^{13}C_{16}]$-tripalmitin, or $[U-^{13}C_{18}]$-triolein.

4. The method of claim 1, wherein said $[^{13}C]$-labeled fatty acid formed after digestion of said $[^{13}C]$-labeled triglyceride is $[1-^{13}C]$-palmitic acid, $[1-^{13}C]$-oleic acid, $[U-^{13}C_{16}]$-palmitic acid, or $[U-^{13}C_{18}]$-oleic acid.

5. The method of claim 1, wherein said individual has cystic fibrosis.

6. The method of claim 1, wherein said biological sample is blood or plasma.

7. A method for obtaining fat digestibility profile in an individual, comprising the steps of:
    orally administering a meal comprising a $[^{13}C]$-labeled triglyceride and a $[^{2}H]$-labeled free fatty acid tracer to said individual;
    measuring the amount of $[^{13}C]$-labeled fatty acid formed after digestion of said $[^{13}C]$-labeled triglyceride and measuring the amount of $[^{2}H]$-labeled free fatty acid tracer in a biological sample of said individual to determine a ratio of $[^{13}C]$-labeled fatty acid to $[^{2}H]$-labeled free fatty acid tracer; and
    repeating said measuring step one or more times to provide a fat digestibility profile for said individual.

8. The method of claim 7, wherein said $[^{2}H]$-labeled free fatty acid tracer is $[2,2-^{2}H_{2}]$-palmitic acid, $[2,2-^{2}H_{2}]$-oleic acid, or $(7,7,8,8-D_{4})$palmitic acid.

9. The method of claim 7, wherein said $[^{13}C]$-labeled triglyceride is $[1,1,1-^{13}C_{3}]$-tripalmitin, $[1,1,1-^{13}C_{3}]$-triolein, $[U-^{13}C_{16}]$-tripalmitin, or $[U-^{13}C_{18}]$-triolein.

* * * * *